United States Patent [19]

Higginbotham

[11] Patent Number: 5,096,114
[45] Date of Patent: Mar. 17, 1992

[54] DISPOSABLE CONTAINER FOR HAZARDOUS WASTE PRODUCTS

[75] Inventor: David D. Higginbotham, Bent Mountain, Va.

[73] Assignee: Corrugated Container Corporation, Roanoke, Va.

[21] Appl. No.: 501,498

[22] Filed: Mar. 30, 1990

[51] Int. Cl.⁵ .......................... B65D 5/46; B65D 5/66
[52] U.S. Cl. ................................ 229/117.15; 206/366; 229/149; 229/150; 229/907
[58] Field of Search ............... 206/366; 229/117.14, 229/117.15, 149, 150, 151, 155, 907, 911

[56] References Cited

U.S. PATENT DOCUMENTS

| | | | |
|---|---|---|---|
| 2,596,087 | 5/1952 | Shoudy | 229/117.14 |
| 2,832,527 | 4/1958 | Bosche, Jr. | 229/149 |
| 3,140,813 | 7/1964 | Hall et al. | 229/150 |
| 3,521,741 | 7/1970 | Beaudry | 229/150 |
| 4,121,755 | 10/1978 | Meseke et al. | 206/366 |
| 4,981,254 | 1/1991 | Pepper | 229/117.14 |

FOREIGN PATENT DOCUMENTS 2085409 4/1982 United Kingdom ................ 206/366

Primary Examiner—Gary E. Elkins
Attorney, Agent, or Firm—Dennison, Meserole, Pollack & Scheiner

[57] ABSTRACT

A portable disposable container comprising a top closure including two inner centrally apertured panels independently lockable across the open upper end of the container in overlying relation to each other. An imperforate closure panel includes a remote handle flap for manipulation of the top container. The closure panel, upon a closing of the container, overlies the inner panels, sealing the openings therein. The handle flap is positioned immediately adjacent a similarly configured handle panel and is locked thereto by a locking extension wrapped about both handles components.

20 Claims, 3 Drawing Sheets

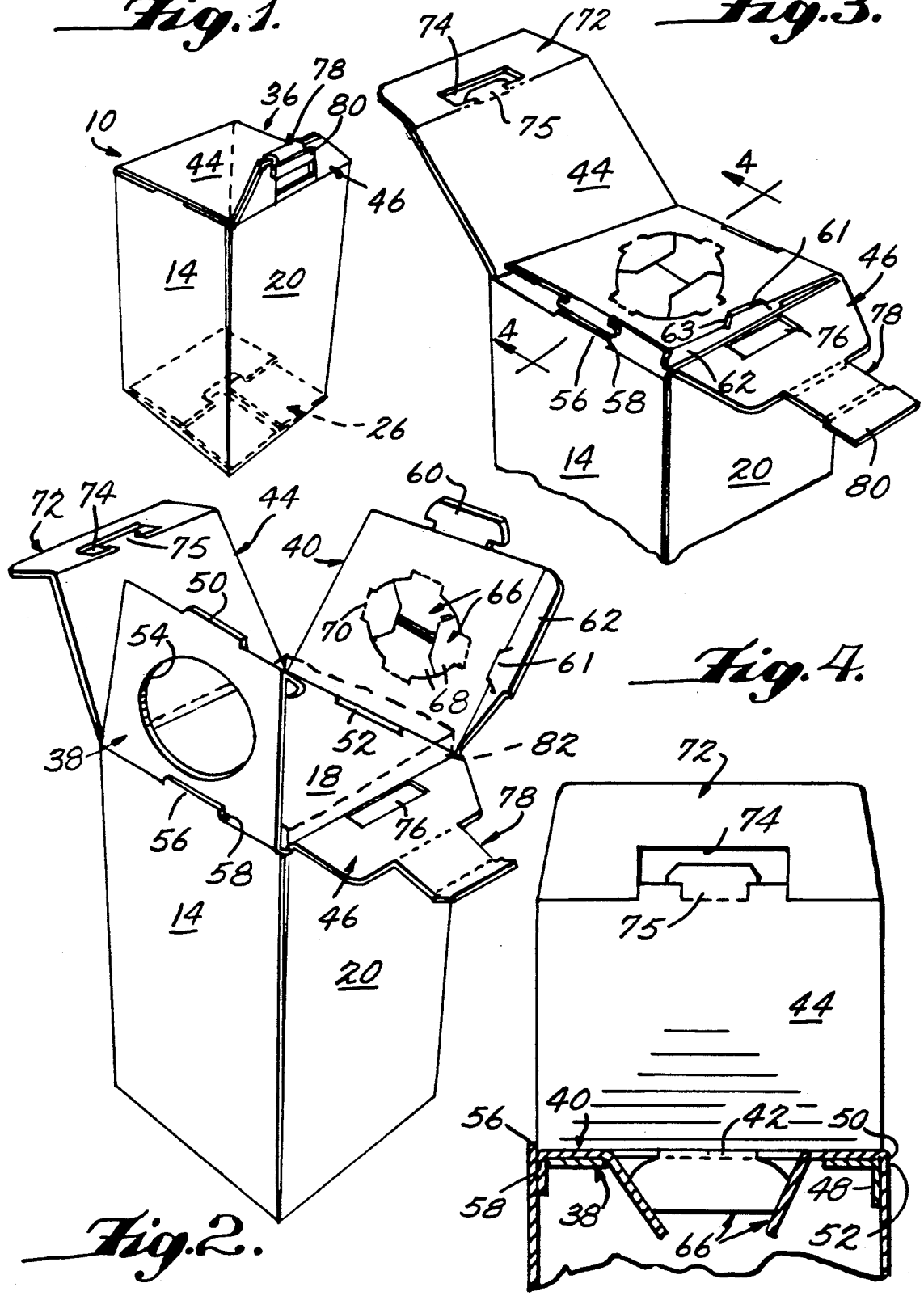

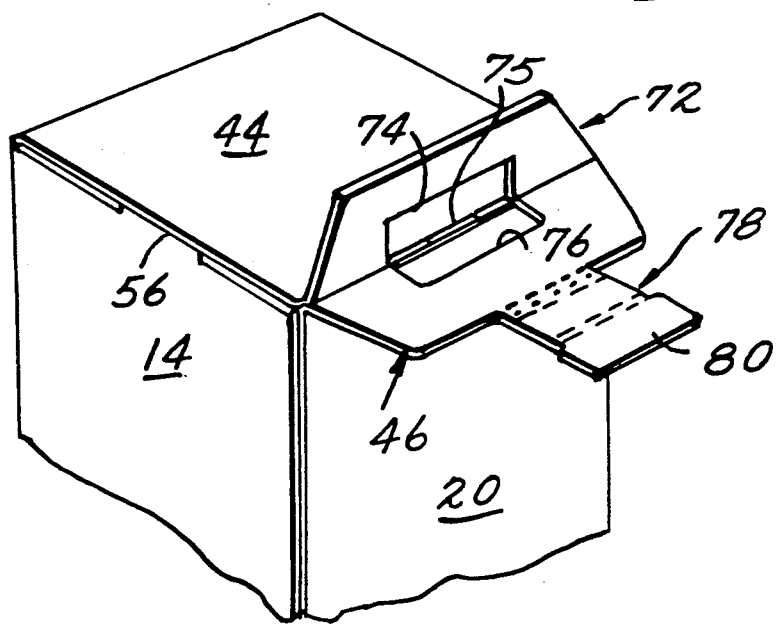
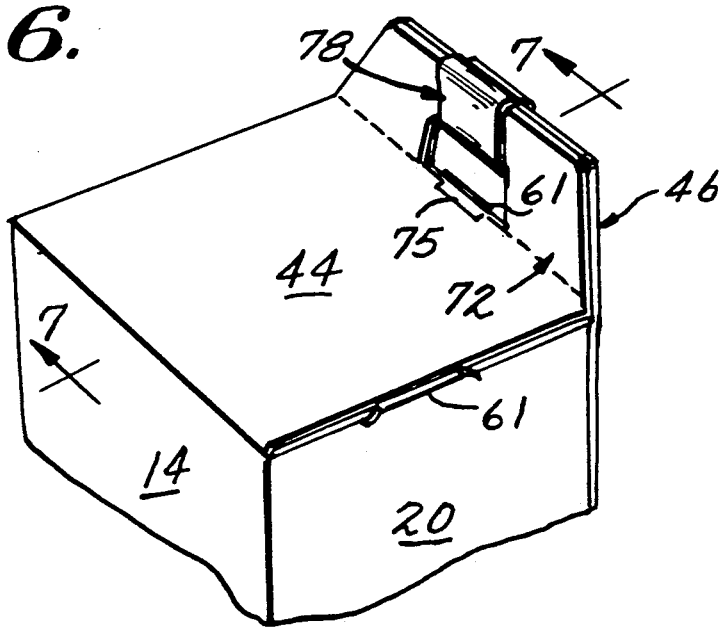
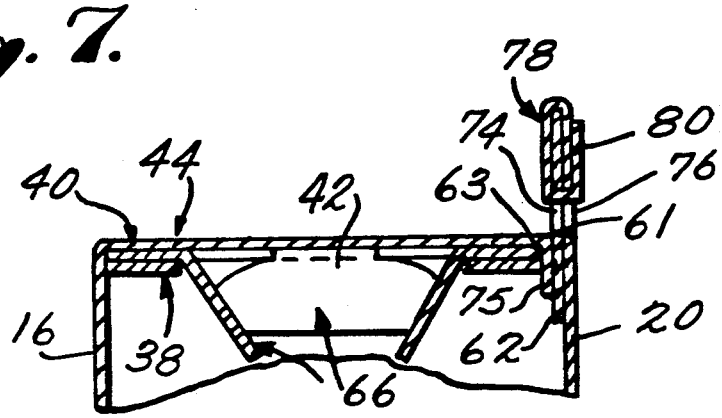

DISPOSABLE CONTAINER FOR HAZARDOUS WASTE PRODUCTS

BACKGROUND OF THE INVENTION

The invention broadly relates to the disposal of contaminated or hazardous waste of the type normally found in hospital environments. Such wastes include sharp or pointed objects such as hypodermic needles, body fluids and tissue, wound dressings, and other matter which must be safely segregated in manner which avoids any personal contact therewith.

For both safety and convenience, recent efforts in this area have involved the utilization of containers which, after having received the waste material, are disposed of in their entirety. Such containers consist of sturdy cartons of corrugated cardboard or the like with an internal plastic bag and, if desired, a bag-stabilizing liner. An example of such a construction will be noted in U.S. Pat. No. 4,863,052, issued Sept. 5, 1989 to Lambert. The plastic bag provides protection against leakage while the cardboard container, as well as the inner liner thereof also normally of cardboard, provide for an effective retention of the sharp items until such time as the entire container can be incinerated.

In the environment of use of container or receptacle for contaminated materials, the container remains open for the convenient introduction of the waste materials, and is only finally sealed when the container is to be readied for disposal. The open container, either accidentally or intentionally, is on occasion moved or shifted. As such, with existing containers there is the possibility of a disruption in the normally provided restrictive opening through which the waste is introduced, and/or an improper grasping of the container by personnel when an intentional shifting of the open container is undertaken. In both situations, accidental contamination is possible.

Other factors which have been found to affect the practicality of the known disposable containers include the cost, particularly as the container is a single-use throwaway item, the ease of assembly, and the sturdiness of construction.

SUMMARY OF THE INVENTION

The portable container of the present invention is considered a significant advance in the art, the current state of which is exemplified by the Lambert patent.

The container, adapted to receive a liquid-tight bag and, as desired, a liner, is so constructed as to achieve a high degree of stability not only in its closed and sealed condition ready for disposal, but also when assembled and used as an open receptacle. In conjunction therewith, the container of the invention is both easy to assemble and economically attractive in light of the compact nature of the blank and the unique although relatively straight forward blank design which simplifies manufacturing procedures. The relatively smaller nature of the blank, and hence the collapsed box prior to use, reduce shipping and storage space requirements. This is an important consideration in light of the large quantities associated with containers of this type and the anticipated expansion of use thereof for hazardous wastes beyond those encountered in the hospital environment.

The container of the invention is formed from a single die cut blank of shape-sustaining foldable and preferable combustible material. While not limited thereto, the container will normally be constructed of conventional carton-type corrugated board.

The blank is basically of a rectangular configuration and includes four elongate side wall panels, which, upon a folding of the blank, define an elongate tubular configuration, the bottom of which is closed in a conventional manner by a bottom closure of interlocking bottom panels, and the top of which is surrounded by top panels, each integrally hinged to the upper edge of one of the side wall panels and defining a top closure.

The top closure includes opposed lower and upper inner panels which are folded in sequence to overlie each other with each of these inner panels spanning the top of the container and having the free outer edge thereof positively interlocked in position and in a manner which fixes the panels against accidental shifting or movement relative to the container top, for example as waste material is introduced into the container, or as the container is moved. The two inner panels each have central openings therethrough, the upper panel having funnel-defining flaps associated therewith which function both as a means for guiding introduced material and for interlocking the inner panels about the aligned openings.

The top closure further comprises a closure panel and a handle panel. These panels remain open during the use of the container. The closure panel includes, along the outer edge thereof remote from the integrally hinged connection thereof to the corresponding side wall panel, a handle flap with a hand-accommodating aperture therethrough. This handle flap provides a highly convenient and completely safe means for grasping and moving the container while still open and in its in use condition. The remote nature of the handle flap allows it to be conveniently grasped without necessitating an approach of the hand close to the central waste-receiving opening. The other top panel, the handle panel, also includes a handhold defined therethrough. This handhold is immediately adjacent the tubular body, at the hinge line of the corresponding side wall panel, and while available for use in moving the container, will be less likely to be used for this purpose.

When the container is to be closed for disposal, the closure panel is folded thereover to completely overlie the apertured inner panels and position the handle flap immediately adjacent the handle panel with the handholds aligned and subsequently interlocked by a locking flange or extension on the handle panel which wraps through the handholds and locks therein in a manner which provides a positive interlocking of the two handles and a cushioned grip for the hand. The closure panel is also provided with a locking tab centrally along the outer edge thereof which folds downwardly opposite to the handle flap and interlocks with an underlying inner panel. Accidental opening of a closed container is substantially impossible without a destruction of the container. The formation of the handle assembly from top panels associated with diametrically opposed side wall panels, and the interlock of the closure panel to an inner panel which is in turn secured to the remaining side wall panels, provides both substantial strength and a convenient distribution of the load of the filled container.

Other features and advantages of the invention will become apparent from the more detailed description of the invention followed hereinafter.

BRIEF DESCRIPTION OF THE DRAWINGS

FIG. 1 is a perspective view of the closed receptacle ready for disposal, the bottom closure being shown in phantom lines;

FIG. 2 is an enlarged perspective view of the container with the top panels prior to folding;

FIG. 3 is a perspective view of the upper portion of the container with the inner top panels both moved toward the closed positions thereof;

FIG. 4 is a cross-sectional view taken substantially on a plane passing along line 4—4 in FIG. 3 and illustrating the inner top panels in their completely closed position with the funnel flaps inwardly deflected;

FIG. 5 is a perspective view of the upper portion of the container with the closure panel in its fully closed position;

FIG. 6 is a perspective view of the upper portion of the container with the handle panel and handle flap interlocked;

FIG. 7 is a cross-sectional detail taken substantially on a plane passing along line 7—7 in FIG. 6.

DESCRIPTION OF THE PREFERRED EMBODIMENT

Figure 8:
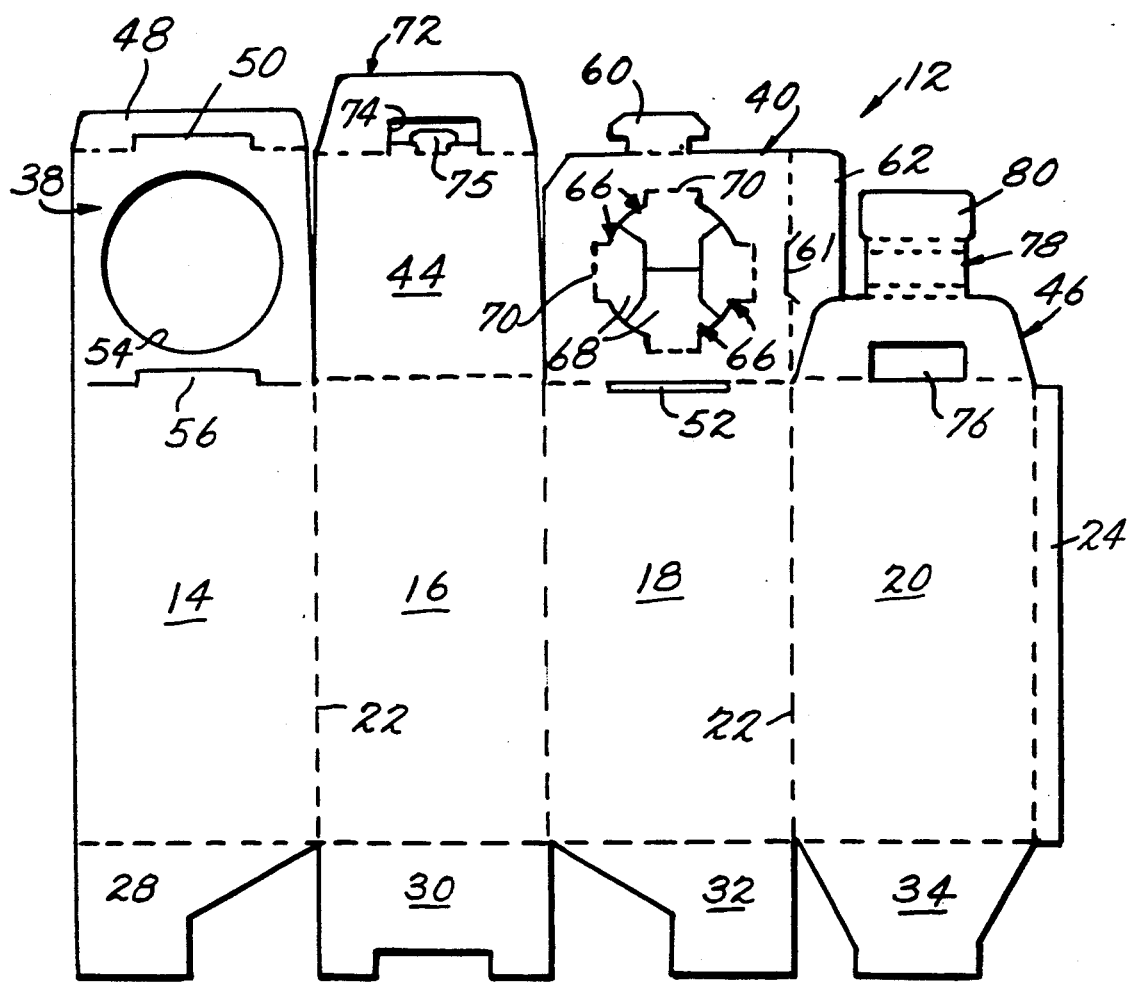
FIG. 8 is a plan view of the one-piece blank from which the container is formed.

Referring now more specifically to the drawing, the portable disposable container 10 is formed from a unitary die cut blank 12. The container 10, closed and ready for disposal preferably by incineration, is illustrated in FIG. 1. The blank, illustrated in FIG. 8, is formed of any appropriate foldable shape sustaining sheet material, preferably corrugated cardboard, fiber board, or the like.

The container 10 includes four vertically elongate rectangular side wall panels, 14, 16, 18 and 20, interconnected by fold lines 22 between adjoining panels. The fold lines 22 in the folded carton form the corners thereof. The endmost wall panel 20 includes a full length joining strip 24 which overlaps and is secured, for example by adhesive, to the opposite endmost panel 14 to define the tubular body of the container. The tubular body is preferably rectangular.

The container 10 further includes a bottom closure 26 conventionally formed of interlocking bottom panels 28, 30, 32 and 34, each respectively hinged along the bottom edge of a corresponding side wall panel.

The top closure 36 of the container 10 includes dual inner top panels 38 and 40 which define the access port 42 for the waste material. The top panels 38 and 40 have inner edges integrally hinged or foldably joined to the opposed side wall panels 14 and 18 along the upper edges thereof.

The top closure further includes a top closure panel 44 integrally hinged to the upper edge of side wall panel 16 between the port-forming panels 38 and 40. Finally, a top handle panel 46 is foldable joined to the upper edge of the end-most side wall panel 20 whereby, upon a forming of the tubular body of the container, the panels 44 and 46 are foldably joined along opposed top edges, as are the panels 38 and 40. As will be readily apparent, full height cut lines are provided between adjacent ones of the top closure forming panels for an independent folding of each.

A full length flange 48 is formed along the remote or outer edge of the top panel 38 and is intregal therewith along a centrally interrupted fold line extending inwardly from the opposed side edges of the panel 38. An elongate tab 50, defined by die cut edges, extends coplanar and integral from the panel 38 and into the flange 48 centrally of the interrupted fold line. So formed, and noting FIG. 2, upon an inward folding of the flange 48, the tab 50 extends outwardly beyond the outer edge of the panel 38. This tab, through the inherent flexibility of the material of the container, snap-locks into a corresponding configured slot 52 defined in the side wall panel 18 immediately below and centrally along the fold-defining upper edge therealong. Noting FIG. 4, the height of the panel 38 is such as to completely overlie the open top of the container with the tab 50 extending well into, and possibly slightly beyond, the receiving slot 52. So formed, the lower one of the two panels defining the access port 42 is rigidly supported across the open top of the container 10 along opposed edges with the flange 48 received within the container. Supported in this manner, it will also be appreciated that a substantial degree of lateral stability is also provided to the upper end of the container by the top panel 38.

In order to form the access port 42, the top panel 38 includes a central circular opening 54 therethrough. The panel 38 is completed by a tab 56 centrally cut therefrom along the fold line at the upper edge of the corresponding side wall 14. This tab 56 is of a length and is positioned similar to the tab 50, and is an integral coplanar extension of the side wall 14. Upon an inward folding of the lower inner panel 38, the vertically retained tab 56 defines or leaves an upwardly directed slot 58 along the hinged edge of the panel 38.

The upper one of the inner top panels, panel 40, includes along the free outer edge thereof, a T-shaped tab 60 integrally hinged or folded thereto. The enlarged head of tab 60, through the flexible or compressible nature of the material, is forcibly engageable through the relatively narrower upwardly directed slot 58 upon a folding of this upper panel 40 over the lower panel 38. Engaged in this manner, the upper panel 40 is locked in position and also positively supported along opposed edges thereof for a further stabilization of the container and particularly the top thereof.

The upper panel 40 includes a foldable flange 62 along the edge thereof adjacent the handle panel 46. This flange 62 inwardly folds for reception within the container and, as with the flange 48, provides additional stability to the container 10, and in particular the upper portion thereof. A tab 61, coplanar with the flange 62, is die cut from the panel 40 centrally along the fold line therebetween. This tab 61 upon a folding of the flange 62, defines an upwardly directed slot 63 in the panel 40 centrally along the side edge thereof adjacent the flange 62.

In order to complete the access port 42, the panel 40 is provided with four inwardly foldable funnel-forming flaps 66 in diametrically opposed pairs at 90 degrees to each other and defining, upon an opening thereof, a circular opening aligned immediately over and complementing the opening 54 in the panel 38. Each of the flaps 66 includes an arcuate portion 68 corresponding to a segment of the formed opening and die cut to individually fold down about fold lines 70 positioned immediately outward of the formed circle or circular opening.

Each of the arcuate flap portions 68 extends laterally to each side of the corresponding fold line 70. Upon a downward folding thereof through the underlying opening 54, these portions 68 define a general funnel-shaped configuration and slightly underlie the periphery of the lower opening 54 in a manner tending to centrally interlock the overlying panels 40 and 38. As will be appreciated from the drawings, the die cutting of the funnel flaps 66 is such whereby one opposed pair include inner extensions which, together, span the "circle" and are separated by a single cut line therebetween.

The top closure panel 44 is imperforate and includes, along the outer edge thereof, a handle flap or flange 72 joined thereto along an intregal hinge or fold line. The handle flap has a hand-accommodating aperture 74 defined therein centrally along the fold line. When the container is to be closed for disposal, the closure panel 44 is folded over the two inner panels 38 and 40, spanning completely across the top of the container 10 with the handle flap 72 upwardly turned immediately inward of the opposed side wall panel 20, as shown in FIG. 5.

In order to lock the closure panel 44 in its closed position, an integral T-shaped locking tab 75 is formed along the handle flange fold line and extends into the handhold aperture 74. This locking tab 75, upon a closing of the panel 44, is folded downward and forcibly engaged through slot 63. The tab 75, and in particular the enlarged head portion thereof, will compress slightly for engagement through the relatively smaller slot 63. Once through the slot the looking tab will return to its original shape for an effective resistance to withdrawal. The closure panel 44 is thus effectively retained in its closed position.

The handle panel 46 is of substantially the same size and shape as the handle flap 72, including slightly tapered opposed edges with rounded outer corners. Noting FIGS. 6 and 7, the handle panel 46 is positioned to parallel the vertically extending handle flap 72 in intimate engagement therewith. As will be appreciated, the handle panel 46 also includes a hand-accommodating aperture 76 therein centrally along the fold line between the handle panel 46 and the side wall panel 20 to align with and complement the aperture 74 in the handle flap 72.

In order to further secure the closure panel 44 and complete the top closure, the handle panel 46 is locked to the handle flap 72 by a locking flap or extension 78 formed integral with the outer edge of the handle panel 46 along a fold line therebetween and in alignment with the hand-accommodating aperture 76. This locking extension includes an outer end portion 80 of a slightly greater width than that of the hand apertures 74 and 76 for a forcible engagement therethrough. The height of the locking flap 78, that is the length thereof outward from the outer edge of the handle panel 46, is such as to wrap over the upper or outer edges of the adjacent handle panel 46 and handle flap 72, pass downwardly therefrom and extend the enlarged outer end 80 through the aligned apertures 74 and 76 and up along the outer face of the handle panel 46. The locking extension 78 is provided with appropriate relatively wide fold lines so as to fold about the aligned upper edges of the panel and flap and the upper edges of the corresponding apertures 74 and 76 with the forced engagement with the enlarged outer or head end portion 80 locking the locking flap in its handle-securing position. As will be appreciated, smooth upper and lower gripping edges are provided by the folded locking flap 78 with the engagement of the hand therewith further stabilizing the formed handle. It will also be recognized that the handle, formed as above described, consists of two components respectively engaged with opposed sides of the container for a highly stable support of the container when removed for disposal.

In use, the container may be assembled for shipping by adhesively bonding, stapling, or otherwise securing the glue strip 24 to the side wall panel 14 at the opposite end of the blank 12, thus forming a collapsible carton which can be shipped and stored flat. At the point of use, the bottom panels will be interlocked in a conventional manner to provide a vertical container which, as desired, can be provided with an internal fluid-tight plastic bag 82 with or without a bag stabilizing internal liner. The container will, at this stage, appear as illustrated in FIG. 2. Noting the sequence of FIGS. 2, 3 and 4, the lower top panel 38 is folded horizontally across the upper end of the container 10 and the tab 50 thereof locked into the opposed slot 52. This fixes the position of the panel 38 and stabilizes the upper end of the container. The upper panel 40 of the inner panels is then folded over the lower panel 38 with the side flange 62 slid along one edge of the panel 38 and with the locking tab 60 force-engaged through the slot 58, thus similarly locking the panel 40 in position with the opposed edges thereof fully supported and with the panel 40 in turn further stabilizing the upper portion of the container 10.

The access port 42 is then defined by downwardly folding the funnel flaps 66, preferably to slightly engage beneath the panel 38 at points about the central opening 54 therein for an interlocking of the panels about the access port. The container, thus formed, is rigidly constructed and ready for use in the reception of waste material through the formed access port.

In this position of use, and noting FIGS. 3 and 4 in particular, it is significant that the top closure panel 44, outwardly extending to allow free access to the access port 42, positions the handle flap 72 remote from the waste-receiving opening into the interior of the container. This is important in that the container, during use, can, through the handle flap 72, be easily grasped and moved, generally by sliding, from one location to another as demanded by circumstances. The remote nature of the handle flap 72, when the container is in its waste-receiving configuration, ensures an avoidance of any engagement with the contaminated materials within the container or with the container itself adjacent port. The formation of the handle flap 72 as a complete "handle" with a hand-accommodating aperture, ensures that one using this flap as a means to move the open container will have a positive grasp thereon. It will also be recognized that the positive interlocking of the two inner panels 38 and 40 allow for a movement of the open container without affecting the stability of the container or the security of the panels 38 and 40.

After the container has been filled, or the use thereof is complete, the top closure panel 44, by means of the handle flap 72, is swung over the access port 42 and the locking tab 75 engaged through slot 63, thus closing and sealing the port. The handle panel 46 is then upwardly pivoted and locked to the handle flap by the locking extension 78. It is of interest to note that the locking extension 78, as it folds about the two handle elements, exposes that surface of the locking extension which is the most remote from the access port during the use thereof, thus further reducing any possibility of direct contact with contaminated materials.

From the foregoing, it will be recognized that the container of the invention constitutes a particularly significant advance in providing a means for conveniently and safely disposing of contaminated or hazardous wastes. The specific embodiment illustrated is for the purpose of setting forth the principles of the invention. Modifications and variations as may occur to those skilled in the art are to be considered within the scope of the invention set forth in the attached claims.

I claim:

1. A disposable container for waste products, said container comprising:

a bottom closure and side panels with upper edges defining an open container top;

a top closure comprising opposed first and second top panels with inner edges hingedly secured to respective first and second opposed side panels at the upper edges thereof, said top panels having remote outer edges;

said first top panel being adapted to overlie said open container top and including locking means on the outer edge thereof, and cooperating locking means adjacent the upper edge of said second side panel for receiving said locking means of said first top panel and fixing the position of said first top panel across the open top of said container;

said second top panel being adapted to overlie said first top panel and said open container top, said second top panel including locking means on the outer edge thereof and cooperating locking means adjacent the upper edge of said first side panel for receiving said locking means of said second top panel and fixing the position of said second top panel across said open top;

said first and second top panels, upon engagement of the respective locking mans, being rigidly positioned across said open container top and stabilizing said container at said open top thereof;

each of said first and second top panels including a central opening therethrough, said central openings aligning with each other when said first and second top panels overlie said open top to define an access port through said first and second top panels and into said container for the reception of waste products, and a third top panel hingedly secured to a third side panel and extending therefrom to a remote outer edge, a handle flap on said remote outer edge of said third top panel defining a handhold remote from the open top of said container for enabling a manual grasping and moving of said container without direct exposure to said access port, said third top panel being of a width sufficient to span the open top of the container, said third top panel being imperforate and defining a closure panel adapted to overlie and close said access port with said handle flap positioned adjacent and extending beyond a fourth side panel opposite said third side panel.

2. The container of claim 1 including a fourth top panel hingedly secured to the upper edge of said fourth side panel and projecting therefrom to lie adjacent said handle flap when said closure panel overlies said access port, said fourth top panel comprising a handle panel, said handle panel and said handle flap being of complementary configuration and combining to define a container handle directly secured to both said closure panel and said fourth side panel.

3. The container of claim 2 wherein each of said handle panel and said handle flap includes a hand-accommodating accommodating aperture therethrough, said apertures aligning with each other in the defined handle, said handle panel including an outer edge, an elongate foldable extension extending from said outer edge of said handle panel, said extension engaging about said handle and through the aligned apertures to lock said handle panel to said handle flap.

4. The container of claim 3 wherein said extension includes an outer end portion of a width slightly greater than the width of said apertures and is flexibly deformable for forced engagement through said apertures trough a flexing thereof and in a manner to preclude accidental withdrawal therefrom.

5. The container of claim 4 wherein said second top panel has the opening therein defined by hingedly secured flaps foldable through the opening in said first top panel and defining an inwardly directed funnel configuration through the opening in the first top panel and into the container.

6. The container of claim 5 wherein said funnel forming flaps lock to said first top panel about the opening therein.

7. The container of claim 2 wherein said side panels define a rectangular container with said first and second side panels being at right angles to said third and fourth side panels.

8. The container of claim 7 wherein said container is formed from a single blank of shape-sustaining foldable material.

9. A disposable container for waste products, said container comprising:

a bottom closure and side panels with upper edges defining an open container top;

a top closure comprising opposed first and second top panels with inner edges hingedly secured to respective first and second opposed side panels at the upper edges thereof, said top panels having remote outer edges;

said first top panel being adapted to overlie said open container top and including locking means on the outer edge thereof, and cooperating locking means adjacent the upper edge of said second side panel for receiving said locking means of said first top panel and fixing the position of said first top panel across the open top of said container;

said second top panel being adapted to overlie said first top panel and said open container top, said second top panel including locking means on the outer edge thereof and cooperating locking means adjacent the upper edge of said first side panel for receiving said locking means of said second top panel and fixing the position of said second top panel across said open top;

said first and second top panels, upon engagement of the respective locking means, being rigidly positioned across said open container top and stabilizing said container at said open top thereof;

each of said first and second top panels including a central opening therethrough, said central openings aligning with each other when said first and second top panels overlie said open top to define an access port through said first and second top panels and into said container for the reception of waster products; and a closure panel hingedly secured to a third one of said side panels and adapted to overlie said first and second top panels, said closure panel being imperforate and closing said access port, said closure panel having a remote edge, and locking means securing the remote edge of said closure panel adjacent to a fourth one of side panels remote from said third side panel to which said closure panel is secured.

10. The container of claim 9 including a handle flap on the remote edge of said closure panel, and a handle panel on said fourth side panel complementary to said handle flap, and positionable immediately adjacent the handle flap with the closure panel overlying said access port, and means securing said handle panel to said handle flap to define a container handle.

11. A portable container for the reception of waste materials, said container comprising:
a bottom closure and a peripheral side wall with an upper edge defining an open top to said container;
a top closure including top panel means for overlying said container open top, said top panel means being foldably secured to said upper edge for movement to a position overlying said container open top;
lock means for fixing said top panel means to said peripheral wall overlying said open top and against movement relative thereto, said top panel means including an access port defined centrally therethrough into said container;
said top closure further including a closure panel having a first edge foldably secured to the upper edge of said side wall for pivoting of said closure panel between a first position outwardly extending relative to the top of the container and a second position intimately overlying and closing said access port, said closure panel having a second outer edge remote from the first edge thereof;
handle means integral with the outer edge of said closure panel and defining a handhold in both positions of said closure panel for movement of said container; and
a handle panel projecting from the upper edge of said side wall and engaging said handle means in the second position of said closure panel, and means for joining said handle means and said handle panel to define a container handle.

12. The container of claim 11 wherein said top panel means comprises a panel having an inner edge integral with the upper edge of the side wall along a fold line and an outer edge including said lock means thereon engageable with the container adjacent the upper edge of the side wall opposite the fold line for fixedly positioning said top panel means across said container open top.

13. The container of claim 11 including locking means on the outer edge of said closure panel for securing said closure panel outer edge to said side wall in the second position of said closure panel.

14. A disposable container for waste products, said container comprising:
a bottom closure and side panels with upper edges defining an open container top;
a top closure comprising first and second top panels with inner edges hingedly secured to respective first and second side panels at the upper edges thereof, said top panels having remote outer edges;
said first top panel being adapted to overlie said open top, said first top panel including locking means for fixing said first top panel in position across the open top of said container;
said second top panel being adapted to overlie said first top panel and said open container top, said second top panel including locking means for fixing the position of said second to panel across said open top;

said first and second top panels, upon engagement of the respective locking means, being rigidly positioned across said open container top and stabilizing said container at said open top thereof;
each of said first and second top panels including a central opening therethrough, said central openings aligning with each other when said first and second top panels overlie said open top to define an access port through said first and second top panels and into said container for the reception of waste products;
a third top panel hingedly secured to a third side panel and extending therefrom to a remote outer edge, and a handle flap on said remote outer edge of said third top panel defining a handhold remote from the open top of said container for enabling a manual grasping and moving of said container without direct exposure to said access port, said third top panel being of a width sufficient to span the open top of the container, said third top panel being imperforate and defining a closure panel adapted to overlie and close said access port; and
a fourth top panel hingedly secured to the upper edge of a fourth side panel and projecting therefrom to lie adjacent said handle flap when said closure panel overlies said access port, said fourth top panel and said handle flap being of complementary configuration and combining to define a container handle directly secured to both the closure panel and said fourth side panel.

15. A disposable container for waste products, said container comprising:
a bottom closure and side panels with upper edges defining an open container top;
a top closure comprising first and second top panels with inner edges hingedly secured to respective first and second side panels at the upper edges thereof, said top panels having remote outer edges;
said first top panel being adapted to overlie said open top, said first top panel including locking means for fixing said first top panel in position across the open top of said container;
said second top panel being adapted to overlie said first top panel and said open container top, said second top panel including locking means for fixing the position of said second top panel across said open top;
said first and second top panels, upon engagement of the respective locking means, being rigidly positioned across said open container top and stabilizing said container at said open top thereof;
each of said first and second top panels including a central opening therethrough, said central openings aligning with each other when said first and second top panels overlie said open top to define an access port through said first and second top panels and into said container for the reception of waste products; and
a closure panel hingedly secured to a third one of said side panels and adapted to overlie said first and second top panels, said closure panel being imperforate, overlying and closing said access port, said closure panel having a remote edge, and locking means securing the remote edge of said closure panel remote from said third side panel to which said closure panel is secured.

16. The container of claim 15, including a handle flap on the remote edge of said closure panel, and a handle panel on a fourth side panel complementary to said handle flap and positionable immediately adjacent the handle flap with the closure panel overlying said access sport, and means securing said handle panel to said handle flap to define a container handle.

17. The container of claim 16 wherein said handle panel and said handle flap each include a hand-accommodating aperture therethrough, said apertures aligning with each other in the defined handle to form a handhold.

18. A portable container for the reception of waste materials, said container comprising:

a bottom closure and a peripheral side wall with an upper edge defining an open top to said container;

a top closure including top panels means for overlying said container open top, said top panel means being foldably secured to said upper edge for movement to a position overlying said container open top, said top panel means, when overlying said container open top, defining an access port;

said top closure further including a closure panel having a first edge foldably secured to the upper edge of said side wall for pivoting of said closure panel between a first position outwardly extending relative to the top of the container and a second position intimately overlying and closing said access port, said closure panel having a second outer edge remote from said first edge thereof;

a handle flap integral with the remote edge of said closure panel and defining a handhold in both positions of said closure panel for movement of said container; and a handle panel projecting from the upper edge of said side wall and engaging said handle flap in the second position of said closure panel, and means for joining said handle flap and said handle panel to define a container handle.

19. The container of claim 18 including locking means on the remote edge of said closure panel for securing said remote edge to said side wall in the second position of said closure panel.

20. The container of claim 18 wherein said handle panel and said handle flap each include a hand-accommodating aperture therethrough, said apertures aligning with each other in the defined handle.

* * * * *